United States Patent [19]
Sherman et al.

[11] Patent Number: 6,053,917
[45] Date of Patent: Apr. 25, 2000

[54] MULTI-AXIAL BONE SCREW ASSEMBLY

[75] Inventors: Michael C. Sherman; Troy Drewry, both of Memphis, Tenn.

[73] Assignee: SDGI Holdings, Inc., Wilmington, Del.

[21] Appl. No.: 09/265,265

[22] Filed: Mar. 9, 1999

Related U.S. Application Data

[63] Continuation of application No. 08/719,005, Sep. 24, 1996, Pat. No. 5,879,350.

[51] Int. Cl.⁷ ....................................................... A61B 17/56
[52] U.S. Cl. .................................. 606/61; 606/72; 606/73
[58] Field of Search .................................. 606/61, 72, 73

[56] References Cited

U.S. PATENT DOCUMENTS

| | | |
|---|---|---|
| 4,763,644 | 8/1988 | Webb . |
| 4,805,602 | 2/1989 | Puno et al. . |
| 4,946,458 | 8/1990 | Harms et al. . |
| 5,005,562 | 4/1991 | Cotrel . |
| 5,176,678 | 1/1993 | Tsou . |
| 5,207,678 | 5/1993 | Harms et al. . |
| 5,261,909 | 11/1993 | Sutterlin et al. . |
| 5,360,431 | 11/1994 | Puno et al. . |
| 5,443,467 | 8/1995 | Biedermann et al. . |
| 5,466,237 | 11/1995 | Byrd, III et al. . |
| 5,474,555 | 12/1995 | Puno et al. . |
| 5,476,464 | 12/1995 | Metz-Stavenhagen et al. . |
| 5,501,684 | 3/1996 | Schlapfer et al. . |
| 5,520,690 | 5/1996 | Errico et al. . |
| 5,531,746 | 7/1996 | Errico et al. . |
| 5,549,608 | 8/1996 | Errico et al. . |
| 5,554,157 | 9/1996 | Errico et al. . |
| 5,575,792 | 11/1996 | Errico et al. . |
| 5,578,033 | 11/1996 | Errico et al. . |
| 5,584,834 | 12/1996 | Errico et al. . |
| 5,586,984 | 12/1996 | Errico et al. . |
| 5,607,426 | 3/1997 | Ralph et al. ............................... 606/61 |
| 5,609,593 | 3/1997 | Errico et al. . |
| 5,647,873 | 7/1997 | Errico et al. ............................... 606/61 |
| 5,669,911 | 9/1997 | Errico et al. . |
| 5,672,176 | 9/1997 | Harms et al. . |
| 5,733,285 | 3/1998 | Errico et al. ............................... 606/61 |
| 5,817,094 | 10/1998 | Errico et al. ............................... 606/61 |

FOREIGN PATENT DOCUMENTS

| | | |
|---|---|---|
| 195 09 332 | 8/1996 | Germany . |
| 2 173 104 | 10/1996 | United Kingdom . |

OTHER PUBLICATIONS

Protest under 37 C.F.R. Section 1.291, dated Mar. 3, 1997.
Declaration of J.P. Errico Pursuant To Protest Under 37 C.F.R. Section 1.291.
Sofamor Danek Meeting May 2, 1996, entitled Implemedics.

*Primary Examiner*—Michael Buiz
*Assistant Examiner*—Julian W. Woo
*Attorney, Agent, or Firm*—Woodard, Emhardt, Naughton Moriarty & McNett

[57] ABSTRACT

A multi-axial bone screw assembly includes a bone screw having a partially spherical head. The bone screw head is truncated at an upper surface in which a tool receiving recess is defined. The assembly includes a receiver member including a central bore that defines a tapered recess to receive a contracting collet carrying the head of the bone screw. The bore of the receiver member also defines a channel communicating with the recess and configured to receive a spinal rod therein. A portion of the channel is threaded to receive a set screw above the rod. The assembly also includes a contracting collet disposed between the rod and the head of the bone screw. The collet defines a partially spherical recess to receive the head of the bone screw, and includes deflectable fingers that substantially surround the screw head. As the set screw is tightened into the receiver member, the set screw compresses the rod against the collet, which presses the collet into the tapered recess of the receiver member, thereby deflecting the fingers of the collet against the bone screw head.

17 Claims, 2 Drawing Sheets

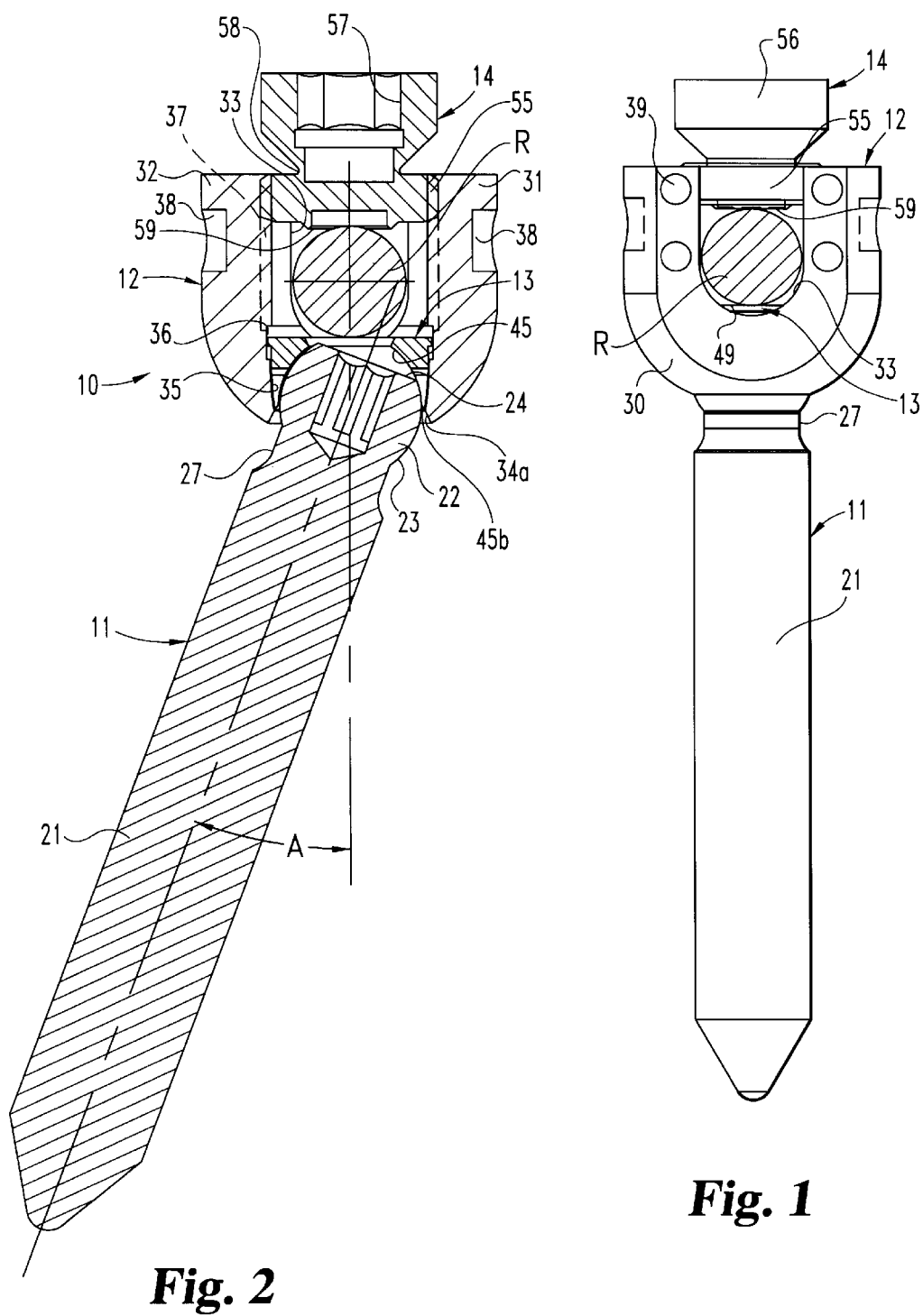

MULTI-AXIAL BONE SCREW ASSEMBLY

This application is a continuation of application Ser. No. 08/719,005, filed Sep. 24, 1996, now U.S. Pat. No. 5,879,350.

BACKGROUND OF THE INVENTION

The present invention concerns a bone screw assembly, particularly useful for engagement in the vertebrae of the spine. In particular, the invention contemplates a bone screw assembly that is capable of achieving multiple angular orientations with respect to an elongated rod extending along the spine.

Several techniques and systems have been developed for correcting and stabilizing the spine and for facilitating fusion at various levels of the spine. In one type of system, a bendable rod is disposed longitudinally along the length of the spine or vertebral column. The rod is preferably bent to correspond to the normal curvature of the spine in the particular region being instrumented. For example, the rod can be bent to form a normal kyphotic curvature for the thoracic region of the spine, or a lordotic curvature for the lumbar region. In accordance with such a system, the rod is engaged to various vertebrae along the length of the spinal column by way of a number of fixation elements. A variety of fixation elements can be provided which are configured to engage specific portions of the vertebra. For instance, one such fixation element is a hook that is configured to engage the laminae of the vertebra. Another very prevalent fixation element is a spinal screw which can be threaded into various aspects of the vertebral bone.

In one typical procedure utilizing a bendable rod, the rod is situated on opposite sides of the spine or spinous processes. A plurality of bone screws are threaded into a portion of several vertebral bodies, very frequently into the pedicles of these vertebrae. The rods are affixed to these plurality of bone screws to apply corrective and stabilizing forces to the spine.

One example of a rod-type spinal fixation system is the TSRH® Spinal System sold by Danek Medical, Inc. The TSRH® System includes elongated rods and a variety of hooks, screws and bolts all configured to create a segmental construct throughout the spine. In one aspect of the TSRH® System, the spinal rod is connected to the various vertebral fixation elements by way of an eyebolt. In this configuration, the fixation elements are engaged to the spinal rod laterally adjacent to the rod. In another aspect of the TSRH® System, a variable angle screw is engaged to the spinal rod by way of an eyebolt. The variable angle screw allows pivoting of the bone screw in a single plane that is parallel to the plane of the spinal rod. Details of this variable angle screw can be found in U.S. Pat. No. 5,261,909 to Sutterlin et al., owned by the Assignee of the present invention. One goal achieved by the TSRH® System is that the surgeon can apply vertebral fixation elements, such as a spinal hook or a bone screw, to the spine in appropriate anatomic positions. The TSRH® System also allows the surgeon to easily engage a bent spinal rod to each of the fixation elements for final tightening.

Another rod-type fixation system is the Cotrel-Dubosset/CD Spinal System sold by Sofamor Danek Group, Inc. Like the TSRH® System, the CD® System provides a variety of fixation elements for engagement between an elongated rod and the spine. In one aspect of the CD® System, the fixation elements themselves include a body that defines a slot within which the spinal rod is received. The slot includes a threaded bore into which a threaded plug is engaged to clamp the rod within the body of the fixation element. The CD® System includes hooks and bone screws with this "open-back" configuration. Details of this technology can be found in U.S. Pat. No. 5,005,562 to Dr. Cotrel. One benefit of this feature of the CD® System is that the fixation element is positioned directly beneath the elongated rod. This helps reduce the overall bulkiness of the implant construct and minimizes the trauma to surrounding tissue.

On the other hand, these fixation elements of the CD® System are capable only of pivoting about the spinal rod to achieve variable angular positions relative to the rod. While this limited range of relative angular positioning is acceptable for many spinal pathologies, many other cases require more creative orientation of a bone screw, for instance, relative to a spinal rod. Certain aspects of this problem are addressed by the variable angle screw of the TSRH® System, as discussed in the '909 Patent. However, there is a need for a bone screw that is capable of angular orientation in multiple planes relative to the spinal rod. Preferably, the bone screw is capable of various three-dimensional orientations with respect to the spinal rod. Screws of this type have been referred to as poly-axial or multi-axial bone screws.

Others have approached the solution to this problem with various poly-axial screw designs. For example, in U.S. Pat. No. 5,466,237 to Byrd et al., a bone screw is described which includes a spherical projection on the top of the bone screw. An externally threaded receiver member supports the bone screw and a spinal rod on top of the spherical projection. An outer nut is tightened onto the receiver member to press the spinal rod against the spherical projection to accommodate various angular orientations of the bone screw relative to the rod. While this particular approach utilizes a minimum of components, the security of the fixation of the bone screw to the rod is lacking. In other words, the engagement or fixation between the small spherical projection on the bone screw and the spinal rod is readily disrupted when the instrumentation is subjected to the high loads of the spine, particularly in the lumbar region.

In another approach shown in U.S. Pat. No. 4,946,458 to Harms et al., a spherical headed bone screw is supported within separate halves of a receiver member. The bottom of the halves are held together by a retaining ring. The top of the receiver halves are compressed about the bone screw by nuts threaded onto a threaded spinal rod. In another approach taken by Harms et al., in U.S. Pat. No. 5,207,678, a receiver member is flexibly connected about a partially spherical head of a bone screw. Conical nuts on opposite sides of the receiver member are threaded onto a threaded rod passing through the receiver. As the conical nuts are threaded toward each other, the receiver member flexibly compresses around the head of the bone screw to clamp the bone screw in its variable angular position. One detriment of the systems in the two Harms et al. patents is that the spinal rod must be threaded in order to accept the compression nuts. It is known that threaded rods can tend to weaken the rods in the face of severe spinal loads. Moreover, the design of the bone screws in the '458 and '678 Patents require a multiplicity of parts and are fairly complicated to achieve complete fixation of the bone screw.

There is therefore a need remaining in the industry for a multi-axial or poly-axial bone screw that can be readily and securely engaged to an elongated spinal rod. Preferably, the spinal rod can be of any configuration—i.e., smooth, roughened, knurled or even threaded. This need also encompasses the need for minimizing the profile and bulk of any of the components used to engage the bone screw to the spinal rod in a variety of angular orientations.

SUMMARY OF THE INVENTION

In one preferred embodiment of the invention, a spinal fixation assembly includes a multi-axial assembly for engaging a bone engaging fastener to an elongated member at a variety of three dimensional angular orientations. In the preferred embodiment, the bone engaging fastener is a bone screw having a lower portion configured for engaging a vertebra, and a head that is at least partially spherical in configuration.

The multi-axial assembly includes a contracting collet that defines a partially spherical recess sized to receive the head of the fastener therein. In one aspect of the invention, the collet includes a lower deflectable portion configured to substantially surround the head of the fastener when the head is disposed within the spherical recess. The deflectable portion can be formed by a plurality of fingers separated by slots. In one feature, the spherical recess defines a recess opening in the bottom of the collet that has a diameter smaller than the diameter of the spherical head of the bone screw. The fingers deflect outward to accept the screw head through the recess opening, and then contract around the screw head when the head is disposed within the spherical recess.

The assembly also includes a receiver member that defines a bore therethrough from a top end to a bottom end. The bore includes a tapered recess for receiving the collet with the head of the fastener disposed within the spherical recess. The receiver member recess also has a lower opening at the bottom end of the receiver member through which the bone engaging portion of the fastener extends. The bore of the receiver member also defines a channel communicating with the recess and having an upper opening at the top end of said receiver member through which the elongated member, or spinal rod, is inserted.

A compression member, or set screw, is provided that engages the bore of the receiver member at the upper opening. The compression member operable to press the rod against the collet, to thereby press the collet into the tapered recess in the receiver member. As the collet is pressed deeper into the recess the deflectable portion, or fingers, of the collet are deflected by the recess against the head of the fastener to fix the head within the spherical recess of the collet.

The present invention provides an assembly that fixes a bone engaging fastener to an elongated member at a plurality of angular orientations relative to the elongated member. The preferred embodiment of a multi-axial bone screw assembly provides the advantage of a solid fixation between a spinal rod and a bone screw, regardless of the angle between the two components.

A further benefit of the present invention resides in the minimum number of components necessary to effect this solid fixation. Another benefit is realized by the deflectable fingers of the contracting collet that enhance the fixation between the components. Other benefits and certain objects of the invention will become apparent upon consideration of the following written description and accompanying figures illustrating one embodiment of the invention.

DESCRIPTION OF THE FIGURES

FIG. 1 is a side elevational view of a multi-axial bone screw assembly in accordance with one embodiment of the present invention, shown engaged to an elongated spinal rod.

FIG. 2 is a cross-sectional view of a multi-axial bone screw assembly as depicted in FIG. 1.

DESCRIPTION OF THE PREFERRED EMBODIMENT

Figure 4:
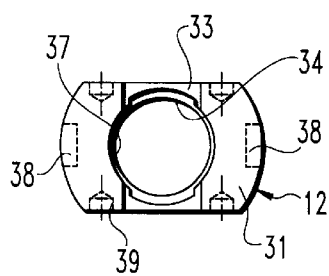
FIG. 4 is a top elevational view of a receiver member used to support the bone screw of FIG. 3 in the multi-axial bone screw assembly of FIGS. 1 and 2.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIGS. 1 and 2, the general components of a multi-axial bone screw assembly 10 in accordance with the present invention are shown. The multi-axial bone screw assembly 10 includes a bone screw 11 configured to engage a bone, such as a vertebra. The assembly further includes a receiver member 12 for supporting the bone screw, a contracting collet 13 for engagement with the bone screw, and a compression member or set screw 14 that is disposed within the receiver member 12 to clamp an elongated member or spinal rod R within the assembly 10.

Figure 3:
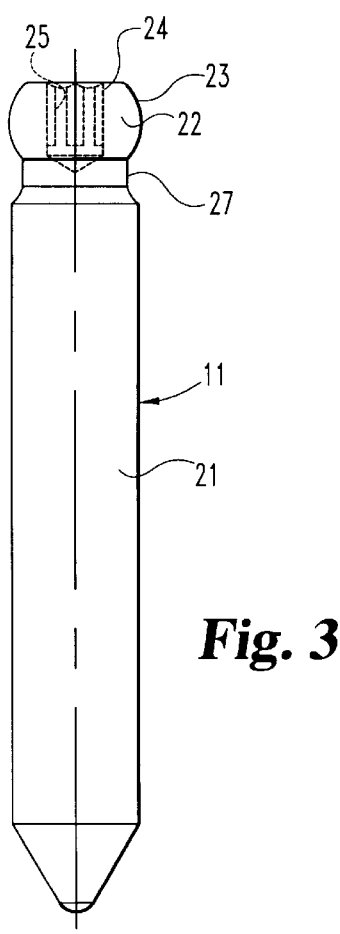
FIG. 3 is a side elevational view of a bone screw for use in the bone screw assembly shown in FIGS. 1 and 2.

In accordance with one aspect of the invention, the bone screw 11 is configured as shown in FIG. 3. In particular, the bone screw 11 includes a threaded shank 21 that preferably carries threads configured to solidly anchor the bone screw within a bone. Most preferably, the threads are cancerous threads, or threads readily adapted for solid fixation within the cancellous bone of the vertebral body. It is understood that the threaded shank 21 can have a variety of configurations depending upon the nature of the bone within which the bone screw 11 is engaged. Moreover, the length of the threaded shank 21 can be adjusted depending upon the bone within which the screw is driven. In one specific embodiment, the threaded shank 21 has a length of about 1.75 inches, and is configured with threads for engagement within the pedicle of a lumbar vertebra.

The bone screw 11 further includes a head 22 at its upper or proximal portion. The head 22 defines a partially spherical outer surface 23. It has been found that a spherical surface is optimum in providing multi-axial angular variations of the position of the bone screw 11 relative to a spinal rod R. In one specific embodiment, the head 22, and specifically the spherical surface 23, resides at a diameter of 0.315 inches. As shown in FIG. 3, the head 22 does not form a complete sphere, having been truncated at an upper surface 24. Again, in a specific embodiment, the head 22 has a height of 0.196 inches as measured between the truncated upper surface 24 and the lower truncation of the head at the transition shank 27.

The head 22 defines a tool receiving recess 25 projecting into the head from the upper surface 24. In one embodiment, the recess 25 is a hex recess to receive a hex end driving tool as is known in the art. It is of course understood that the tool receiving recess 25 can have various configurations, such as a TORX® configuration.

As mentioned above, the head 22 is engaged to the threaded shank 21 of the bone screw 11 by way of a transition shank 27. As shown in FIG. 3 in accordance with the preferred embodiment, the transition shank 27 has a diameter that is less than the diameter of the head 22. As shown in FIG. 2, the reduced diameter transitional shank 27 provides clearance for the bone screw when it is oriented at its greatest angle relative to the receiver member 12. In one specific embodiment, the transition shank 27 has a diameter of 0.236 inches, which is about 0.08 inches smaller than the diameter of the head 22.

Figure 5:
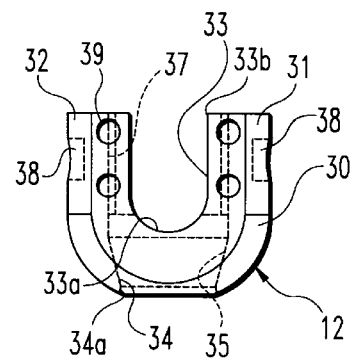
FIG. 5 is a side elevational view of the receiver member shown in FIG. 4.

Referring again to FIG. 2, a receiver member 12 is provided to support both the bone screw head 22 and the spinal rod R. The details of the receiver member 12 can also be seen with reference to FIGS. 4 and 5. In one aspect of the invention, the receiver member 12 includes a U-shaped body 30 defining a first branch 31 and a second branch 32. The branches form a channel 33 between each other. The channel terminates in an edge 33a on opposite sides of the U-shaped body 30. Preferably, the channel 33 has a width that is slightly larger than the diameter of a spinal rod to which the bone screw 11 is to be engaged. The channel 33 has an opening 33b at the top of the member 12 for insertion of the rod R, bone screw 11 and collet 13.

The receiver member 12 further defines a central bore 34 through the body 30. The lowermost portion of the bore 34 defines a slightly tapered recess 35 within which the head 22 of the bone screw 11 and the collet 13 resides, as shown in FIG. 2. The central bore also includes a collet recess 36 that is directly above the tapered recess 35. The collet recess opens into a threaded portion 37 which extends to the top opening 33b of the channel 33. The receiver member 12 is preferably sized for minimal bulk and minimum prominence above the spine. In one specific embodiment, the receiver member has a height of about 0.597 inches. In this specific embodiment, a rod disposed within channel 33 can sit as low as 0.2 inches above the surface of the vertebra when the receiver member 12 contacts the bone.

In one aspect of the receiver member 12, opposite tool recesses 38 are provided in each of the branches 31 and 32. The tool recesses are configured to be engaged by an insertion tool, such as an insertion tool used to insert spinal hooks into the spine. The receiver member 12 can also define a number of gripping holes 39 at the laterally adjacent sides of the body. In the specific illustrated embodiment, four such holes are provided on both sides of the receiver member 12. These gripping holes can be engaged by an appropriately configured gripping tool to support the receiver member 12 during tightening of the bone screw and the other components of the bone screw assembly 10.

In the preferred embodiment, the central bore 34 exits the U-shaped body 30 at a bottom opening 34a. The bottom opening 34a has an upper diameter that is larger than the diameter of the head of the bone screw, but smaller than the outer diameter of the contracting collet 13 when it is engaged around the screw head 22. Consequently, the bone screw can be inserted through the the lower opening 34a of the bore 34 into the recess 35. In one specific embodiment, the lower opening 34a has a diameter of 0.331 inches which is about 0.015 inches larger than the diameter of the bone screw head 22. Preferably, the lower opening 34a is conical or flared outwardly to provide clearance for the transition shank 27 of the bone screw at its largest angled inclination A. In one specific embodiment, the bone screw 11 can move through a range of angles A up to 26°.

The tapered recess 35 expands from the diameter of the lower bore 34a to a larger diameter adjacent the collet recess 36. In one specific embodiment, this larger diameter is 0.349 inches, which is larger than the outer diameter of the head 22 of the bone screw 11. In this specific embodiment, the recess 35 is tapered at an angle of about 4° from the lower opening 34a to the collet recess 36. Again, in the specific embodiment, this tapered recess has a height between the two ends of the recess of about 0.15 inches.

The tapered recess 35 provides a surface against which the contracting collet 13 bears. As the collet 13 is pushed downward towards opening 34a, the tapered recess causes the collet 13 to contract around the screw head 11.

The receiver member 12 is preferably sized for minimal bulk and minimum prominence. In one specific embodiment, the receiver member has a height of 0.582 inches. In the specific embodiment, a rod disposed in the channel 33 can sit as low as 0.19 inches above the vertebra when the receiver member 12 contracts the bone.

The threaded portion 37 of the U-shaped body 30 is configured to engage the set screw 14. In particular, referring to FIG. 2, the set screw 14 includes a threaded plug 55 having threads configured to engage the threaded portion 37 of the receiver member 12. The set screw 14 also includes a driving head 56 that defines a tool recess 57. In this specific embodiment, the tool recess can be a hex recess. Alternatively, the driving head 56 itself can have an external configuration to receive a driving tool. In accordance with the preferred embodiment, the set screw 14 is a "break-off type" set screw in which the driving head 56 is severed from the threaded plug 55 at a shear zone 58. As is known in the art, the head of the break-off set screw will sever at a pre-determined torque, the torque being based upon the resistance offered by the head 22 of the bone screw, collet 13 and the spinal rod R as they are compressed together between the receiver member 12 and the set screw 14.

Figure 6:
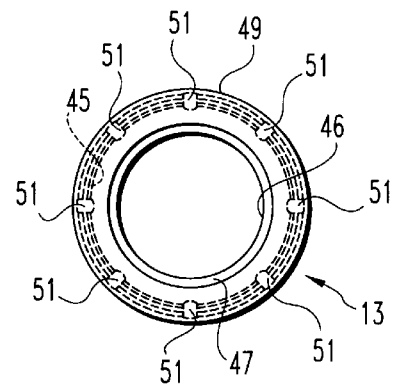
FIG. 6 is a top elevational view of a contracting collet for engagement between the bone screw of FIG. 3 and a spinal rod, in connection with the multi-axial bone screw assembly shown in FIGS. 1 and 2.
Figure 7:
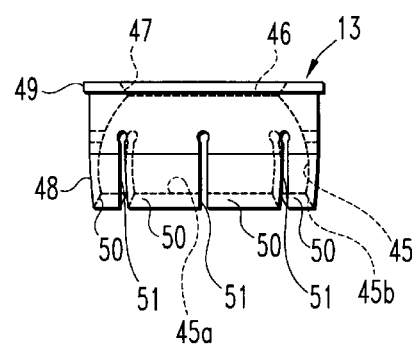
FIG. 7 is a side elevational view of the contracting collet shown in FIG. 6.

In a further aspect of the invention, the bone screw assembly 10 includes a contracting collet 13. The details of the contracting collet are shown in FIGS. 6 and 7. In particular, the contracting collet 13 is hollow and defines a spherical bore 45 at its lower end. As shown in FIG. 2, the head 22 of the bone screw 11 resides substantially within the spherical recess 45 of the contracting collet when the screw assembly 10 is affixed together. The spherical recess 45 is preferably defined at a diameter substantially equal to the diameter of the bone screw head 22. In the specific embodiment, this diameter is 0.315 inches. To permit insertion of the screw head 22 into the spherical recess 45, the recess is truncated at a recess opening 45a at the bottom of the collet. In the preferred embodiment, the recess opening has a diameter less than the diameter of the screw head, most preferably about 0.305 inches. Insertion of the screw head into the recess 45 requires expansion of the opening 45a. A flare 45b facilitates introduction of the screw head 11 into the collet 13. In addition, the lower portion of the collet 13 and spherical recess 45 is formed by a plurality of resilient fingers 50 separated by axial slots 51. The resilient fingers 50 can be urged apart by pressure from the screw head 11 until the head snaps into the recess 45. As shown in FIG. 2, the recess 45 and the recess opening 45a apply constant pressure to the spherical surface 23 of the screw head 11 to hold the head within the collet 13.

The contracting collet 13 further defines a tool insertion bore 46 that can be oriented directly over the tool receiving recess 25 of the bone screw 11 when the bone screw is situated within the receiver member 12. Contracting collet 13 also defines a conical tool relief 47 at the top of the tool insertion bore 46. This relief 47 is oriented at an angle to permit positioning of a driving tool into the head of the bone screw 11 even when the receiver member 12 is not directly aligned with the bone screw.

Contracting collet 13 also forms a conical outer surface 48 that preferably conforms to the tapered recess 35 of the receiver member 12. The collet 13 also includes a rim 49 at its upper end. In accordance with one aspect of the invention, the rim 49 of the contracting collet 13 has a diameter that is slightly smaller than the diameter of the collet recess 36. The diameter of the collet recess 36, and also the rim 49 of the contracting collet 13, is slightly larger than the inner diameter of the threaded portion 37 of the receiver member 12. In this manner, the contracting collet 13 can be retained within the collet recess 36 when the multi-axial bone screw assembly 10 is only loosely connected. In accordance with the preferred embodiment of the invention, the rim 49 can be threaded through the threaded portion 37 of the receiver member 12 from the upper opening 33b of the channel 33 until it is disposed within the collet recess 36. The rim 49 can also be provided with a single thread to mate with the internal threads of the threaded portion 37, to facilitate insertion of the contracting collet 13 into the receiver member 12. In one specific embodiment, the contracting collet has an outer diameter of 0.358 inches at the rim 49. This diameter is about 0.009 inches larger than the inner diameter of the threaded portion 37, and is about 0.012 inches smaller than the diameter of the collet recess 36.

In one embodiment, when the multi-axial bone screw assembly 10 is to be used, in the bone screw 11 can be inserted into a receiver member 12 through the opening 33b so that the screw extends through the bottom opening 34a of the central bore 34. At this point, the receiver member 12 can be supported at the tool recesses 38 by a gripping tool. The tool recess 38 of the bone screw 11 can be engaged by a driving instrument to thread the bone screw 11 into the vertebral bone. Once the bone screw 11 has been driven into its predetermined depth into the bone, the contracting collet 13 can be placed within the receiver member 12 and oriented around the head 22 of the bone screw 11 and within the tapered recess 35. The receiver member 12 can then be engaged by way of the gripping holes 39 by a gripping tool to support the receiver member as the various components of the assembly 10 are tightened against each other. The spinal rod R can be pushed into the upper opening 33b of the channel 33 and into the channel 33.

As the spinal rod R is brought to bear against the contracting collet 13, the collet assumes its final orientation relative to the head 22 of the bone screw 11.

With the spinal rod R in position, the set screw 14 can be threaded into the threaded portion 37 of the receiver member 12. As the set screw 14 is tightened further into the receiver member 12, the tapered recess 35 of the receiver member 12 and the set screw 14 are drawn toward each other. As this process continues, the spinal rod R presses against the top of the contracting collet 13, which then pushes the collet 13 deeper into the tapered recess 35. As the collet advances into the tapered recess 35, the gripping fingers 50 are resiliently pressed against the spherical surface 23 of the screw head 22. The set screw 14 is tightened until the collet 13 and fingers 50 are firmly wedged between the screw head 22 and tapered recess 35. The torque applied to the set screw 14 to drive the rod R into the collet 13 steadily increases until the head 56 of the screw 14 severs at the shear zone 58.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

For example, the specific embodiment of the multi-axial bone screw assembly 10 can be sized for placement at any level of the spine. Of course, it is understood that the relative size of the components of the assembly will be modified for the particular vertebra to be instrumented. Likewise, the relative dimensions of the bone screw and receiver member can be modified to permit greater or lesser degrees of angulation of the bone screw relative to the spinal rod.

In the preferred embodiment, the components of the assembly 10 are formed of stainless steel. It is contemplated that the assembly 10 can be formed of other biocompatible materials, such as titanium, and even materials that permit bone ingrowth.

Further, while the preferred embodiment of the invention concerns a bone screw, other bone fixation members can be adapted to implement the multi-axial capabilities of this invention. For instance, a vertebral hook can be equipped with a spherical head to be clamped to a spinal rod by way of the components of assembly 10.

It is also understood that while the preferred embodiment of the invention engages a bone screw to a rod, various longitudinal members are contemplated. For example, an elongated bar can be disposed within the channel of the receiver member to be clamped between the collet and set screw. The present invention can be applied equally well to smooth rods or bars, or longitudinal members having various surface features, such as knurling or threading.

What is claimed is:

1. A spinal fixation assembly, comprising:

an elongated member configured for placement adjacent and along a length of the spine;

a bone engaging fastener, said fastener having a lower portion configured for engaging a vertebra and an enlarged head;

a collet defining a recess sized to receive at least a portion of said head of said fastener therein, said collet including a lower portion deflectable to substantially surround and engage said portion of said head of said fastener when said head is disposed within said recess, said collet further including an upper portion defining a substantially planar top surface;

a receiver member defining a bore therethrough from a top end to a bottom end, said bore including a lower recess for receiving said collet with said head of said fastener disposed within said recess, said lower recess having a lower opening at said bottom end of said receiver member through which said lower portion of said fastener extends, said receiver member also including a channel communicating with said lower recess said channel being configured to receive said elongated member therein adjacent said recess; and a compression member engaged within said bore, said compression member operable to press said elongated member against said top surface of said collet, to thereby press said collet into said lower recess in said receiver member, whereby as said collet is pressed into said lower recess said deflectable portion of said collet is deflected by said lower recess against said head of said fastener to fix said head within said recess of said collet.

2. The spinal fixation assembly according to claim 1, wherein:

said bore includes an internally threaded portion adjacent said upper opening; and said compression member is a set screw having threads for engagement with said internally threaded portion.

3. The spinal fixation assembly according to claim 1, wherein said head of said bone engaging fastener includes a truncated upper surface, and defines a tool receiving recess through said upper surface.

4. The spinal fixation assembly according to claim 1, wherein said collet includes a bore therethrough, said bore including said recess and a tool insertion bore configured to receive a driving tool to engage said head of said fastener through said bore of said collet.

5. The spinal fixation assembly according to claim 1, wherein said lower recess is tapered from a larger diameter to a smaller diameter at said bottom end.

6. The spinal fixation assembly according to claim 5, wherein said collet includes a conical outer surface configured for complementary engagement with said tapered recess of said receiver member.

7. The spinal fixation assembly according to claim 1, wherein said lower opening of said receiver member is tapered.

8. The spinal fixation assembly according to claim 1, wherein said deflectable portion of said collet includes a plurality of deflectable fingers.

9. The spinal fixation assembly according to claim 1, wherein said collet includes a recess opening at one end of said recess, said recess opening having a diameter smaller than a diameter of said enlarged head of said fastener, whereby said deflectable portion of said collet deflects to receive said fastener head within said recess.

10. The spinal fixation assembly according to claim 9, wherein said recess opening is tapered.

11. A spinal fixation assembly, comprising:

an elongated member configured for placement adjacent and along a length of the spine;

a bone engaging fastener, said fastener having a lower portion configured for engaging a vertebra and a head, said head being at least partially spherical in configuration;

a collet defining a partially spherical recess sized to receive at least a portion of said head of said fastener therein, said collet including a lower contractible portion to substantially surround said head of said fastener when said head is disposed within said spherical recess, and an upper portion having a substantially planar surface and a tapered aperture which communicates with said recess;

a receiver member defining a bore therethrough from a top end to a bottom end, said bore including a recess for receiving said collet with said head of said fastener disposed within said spherical recess, said recess having a lower opening at said bottom end of said receiver member through which said lower portion of said fastener extends, said member also including a channel communicating with said recess and having an upper opening at said top end of said receiver member, said channel being configured to receive said elongated member therein adjacent said recess; and a compression member engaged within said bore at said upper opening, said compression member operable to press said elongated member against said collet, to thereby press said collet into said recess in said receiver member, whereby as said collet is pressed into said recess said contractible portion of said collet is contracted by said recess against said head of said fastener to fix said head within said spherical recess of said collet.

12. The spinal fixation assembly of claim 11, wherein said aperture in said collet is conical.

13. The spinal fixation assembly of claim 11, wherein said contractible portion includes a plurality of deflectable fingers.

14. The spinal fixation assembly of claim 13, wherein said receiver member includes an internally threaded portion adjacent said top end, and said compression member is a set screw having threads configured to engage said threaded portion.

15. The spinal fixation assembly of claim 14, wherein said set screw is a break-off set screw.

16. The spinal fixation assembly of claim 13, wherein said head and said spherical recess have a snap-fit relationship.

17. The spinal fixation assembly of claim 1, wherein said collet upper portion defines a continuous top surface.

* * * * *